(12) United States Patent
Duchaussoy et al.

(10) Patent No.: US 8,703,738 B2
(45) Date of Patent: Apr. 22, 2014

(54) BIOTINYLATED HEXADECASACCHARIDES, PREPARATION AND USE THEREOF

(75) Inventors: Philippe Duchaussoy, Toulouse (FR); Jean Pascal Herault, Frouzins (FR); Jean Marc Herbert, Tournefeuille (FR); Maurice Petitou, Paris (FR); Pierre Savi, Seysses (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/611,753

(22) Filed: Sep. 12, 2012

(65) Prior Publication Data

US 2013/0004551 A1 Jan. 3, 2013

Related U.S. Application Data

(63) Continuation of application No. 12/837,861, filed on Jul. 16, 2010, which is a continuation of application No. 11/684,239, filed on Mar. 9, 2007, now abandoned, which is a continuation of application No. PCT/FR2005/002218, filed on Sep. 7, 2005.

(51) Int. Cl.
*A61K 31/715* (2006.01)

(52) U.S. Cl.
USPC .............................................. 514/54; 514/56

(58) Field of Classification Search
CPC ................................................... A61K 31/715
USPC ..................................................... 514/54, 56
See application file for complete search history.

(56) References Cited

U.S. PATENT DOCUMENTS

| 6,844,329 | B2 | 1/2005 | Duchaussoy et al. |
| 2004/0024197 | A1 | 2/2004 | Duchaussoy et al. |
| 2006/0160768 | A1 | 7/2006 | Duchaussoy et al. |

FOREIGN PATENT DOCUMENTS

| EP | 0 300 099 A1 | 1/1989 |
| EP | 0 529 715 A1 | 3/1993 |
| EP | 0 649 854 A1 | 4/1995 |
| EP | 0 084 999 A1 | 8/1998 |
| WO | WO 98/03554 | 1/1998 |
| WO | WO 9803554 A1 * | 1/1998 |
| WO | WO 99/36428 | 7/1999 |
| WO | WO 99/36443 | 7/1999 |
| WO | WO 9936443 A1 * | 7/1999 |
| WO | WO 02/24754 A1 | 3/2002 |
| WO | WO 0224754 A1 * | 3/2002 |

OTHER PUBLICATIONS

International Search Report dated Feb. 7, 2006 received from the European Patent Office from related International Application No. PCT/FR2005/002218.
U.S. Office Action dated Mar. 29, 2012 from parent U.S. Appl. No. 12/837,861.
U.S. Final Office Action dated Sep. 8, 2011 from parent U.S. Appl. No. 12/837,861.
U.S. Office Action dated Mar. 24, 2011 from parent U.S. Appl. No. 12/837,861.
U.S. Final Office Action dated Jul. 24, 2009 from parent U.S. Appl. No. 11/684,239.
U.S. Office Action dated Oct. 1, 2008 from parent U.S. Appl. No. 11/684,239.
Petitou M. et al., "Introducing a C-Interglycosidic Bond in a Biologically Active Pentasaccharide Hardly Affects its Biological Properties", *Bioorganic & Medicinal Chemistry* 6:1509-1516 (1998).
"The Merck Index", Twelfth edition, 1996, M.N. 920, pp. 151-152.
Van Boeckel C.A.A. et al., "The Unique Antithrombin III Binding Domain of Heparin: A Lead to New Synthetic Antithrombotics", *Angew. Chem. Int. Ed. Engl.* 32(12):1671-1690 (Dec. 1993).
Boons G-J, "Strategies in Oligosaccharide Synthesis", *Tetrahedron* 52(4):1095-1121 (1996).
Paulsen H., "Advances in Selective Chemical Syntheses of Complex Oligosaccharides", *Angew. Chem. Int. Ed. Engl.* 21(3):155-173 (Mar. 1982).
Herbert J.M. et al., "SR123781A, a Synthetic Heparin Mimetic", *Thromb Haemost* 85(5):852-860 (2001).
Herbert J.M. et al., "Biochemical and Pharmacological Properties of SANORG 34006, a Potent and Long-Acting Synthetic Pentasaccharide", *Blood* 91(11):4197-4205 (1998).
Brill W.K-D. et al., "Opening of Levoglucosane Derived Epoxides with Oxygen, Nitrogen and Sulfur Nucleophiles", *Tetrahedron Letters* 39:787-790 (1998).
U.S. Final Official Action dated Feb. 22, 2013 from related U.S. Appl. No. 12/837,861.

* cited by examiner

*Primary Examiner* — Patrick Lewis
*Assistant Examiner* — Everett White
(74) *Attorney, Agent, or Firm* — Scully, Scott, Murphy & Presser, P.C.

(57) ABSTRACT

The invention concerns novel biotinylated hexadecasaccharides of general formula (I) wherein: Biot is a biotin derivative; R, $R_1$ and $R_2$, represent independently of one another a $C_1$-$C_6$ alkoxy or and —$OSO_3^-$; $R_3$ represents a $C_1$-$C_6$ alkoxy or an —$OSO_3^-$, or $R_3$ constitutes a —O—$CH_2$— bridge; Pe represents a saccharide concatenation; as well as their pharmaceutically acceptable salts, and their use as medicines.

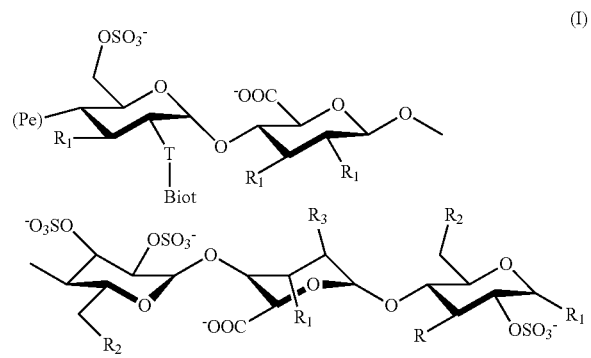

3 Claims, No Drawings

BIOTINYLATED HEXADECASACCHARIDES, PREPARATION AND USE THEREOF

CROSS REFERENCE TO RELATED APPLICATIONS

The present application is a continuation of co-pending application having U.S. Ser. No. 12/837,861, filed on Jul. 16, 2010, which is a continuation of co-pending application having U.S. Ser. No. 11/684,239, filed on Mar. 9, 2007, which is continuation of International Serial No. PCT/FR05/02218, filed on Sep. 7, 2005, which claims benefit of French Application No. 0409557, filed on Sep. 9, 2004, the contents of all of which are incorporated herein by reference.

The present invention relates to novel synthetic biotinylated hexadecasaccharides having the anticoagulant and antithrombotic pharmacological activities of heparin.

Heparin catalyses, especially via antithrombin III (AT III), the inhibition of two enzymes that are involved in the blood clotting cascade, namely factor Xa and factor IIa (or thrombin). Low molecular weight heparin (LMWH) preparations contain chains formed from 4 to 30 monosaccharides and have the property of acting more selectively on factor Xa than on thrombin.

It is known that the inhibition of factor Xa requires binding of heparin to AT III via the antithrombin binding domain (Domain-A) and that the inhibition of factor IIa (thrombin) requires binding to AT III, via the Domain-A, and also to thrombin via a less well defined binding domain (Domain-T).

Synthetic oligosaccharides corresponding to the Domain-A of heparin are known. They are described, for example, in patents EP 84999 and EP 529 715, the patent application published under the number WO 99/36428 and the publication *Bioorg. Med. Chem.* (1998), 6, pp. 1509-1516. These synthetic oligosaccharides have the property of selectively inhibiting, via AT III, the clotting factor Xa without having any activity on thrombin. They show antithrombotic activity in venous thrombosis.

Synthetic oligosaccharides capable of inhibiting thrombin and factor Xa via activation of AT III have been described in the patent applications published under the numbers WO 98/03554 and WO 99/36443.

These patent applications describe novel, biologically active sulfated and alkylated polysaccharide derivatives. They are in particular anticoagulant and antithrombotic. It has in particular been shown that these sulfated and alkylated polysaccharides can be powerful antithrombotic and anticoagulant agents depending on the arrangement of the alkyl groups and sulfate groups borne by the carbohydrate backbone. More generally, it has been found that, by preparing polysaccharide sequences, it is possible to precisely modify the activities of GAG type to obtain highly active products presenting the anticoagulant and antithrombotic pharmacological properties of heparin. In comparison with heparin, they have the advantage of having a determined structure and of not reacting with platelet factor 4, the cause of the thrombocytopaenic effects of heparin.

However, the use in human therapeutics of some of the products described in the patent applications published under the numbers WO 98/03554 and WO 99/36443 and in patent EP 529 715 can prove to be problematic, in particular if these products have a long half-life. In the field of the prevention or treatment of thrombosis with the above products, the fluidity of the blood has to be reestablished or maintained while at the same time preventing the onset of a haemorrhage.

This is because it is well known that a haemorrhage can be triggered in a patient under treatment, for any accidental reason. It may also be necessary to intervene surgically in the case of a patient under antithrombotic treatment. Furthermore, during certain surgical procedures, anticoagulants may be used at a high dose so as to prevent the blood from clotting, and it is necessary to neutralize them at the end of the operation. It is therefore advantageous to have antithrombotic agents that can be neutralized in order to stop the anticoagulant activity at any time. However, the known synthetic oligosaccharides described above cannot easily be neutralized by the known antidotes for heparin or LMWHs, including protamine sulfate.

The present invention relates to novel synthetic biotinylated hexadecasaccharides similar in structure to the compounds described in the patent application published under the number WO 02/24754. The hexadecasaccharides of the invention, and also certain compounds described in document WO 02/24754, are covalently bonded to a biotin derivative (hexahydro-2-oxo-1H-thieno[3,4-d]imidazole-4-pentanoic acid) via a "spacer"—sequences of formula ($T_1$) or ($T_2$) as defined in the present patent application—and consequently have the advantage of being able to be rapidly neutralized by a specific antidote, in an emergency situation. This specific antidote is avidin ("The Merck Index", Twelfth edition, 1996, M.N. 920, pp. 151-152) or streptavidin, two tetrameric proteins with respective masses equal to approximately 66 000 and 60 000 Da, which have very high affinity for biotin.

However, surprisingly, it appears that the length of the "spacer" linking the biotin derivative to the hexadecasaccharide chain, and also the position of the biotin on the saccharide unit are factors that influence the efficacy of the neutralization by a specific antidote, and especially, for example, by avidin. Thus, the hexadecasaccharide compounds according to the invention have a much higher capacity for neutralization by a specific antidote than those described in the patent application published under the number WO 02/24754, by virtue of a "spacer" of controlled size and the position of the biotin on the saccharide unit.

One subject of the present invention is biotinylated hexadecasaccharides of general formula I:

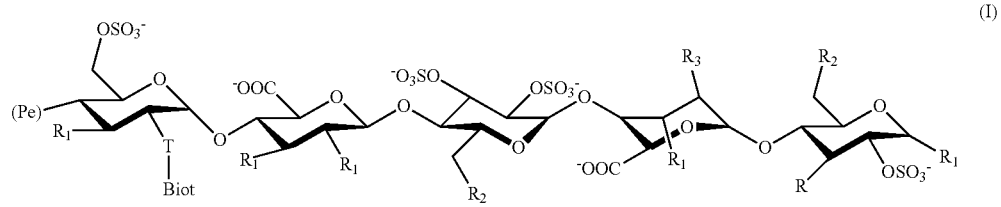

in which:
T represents a sequence $T_1$ or $T_2$ having the following formulae:

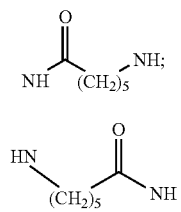
(T₁)

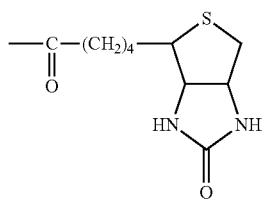
(T₂)

Biot represents the group:

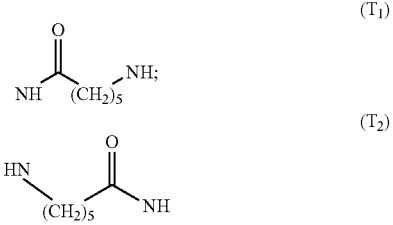

R represents a $(C_1-C_6)$alkoxy radical, especially a methoxy radical, or an —$OSO_3^-$ radical, $R_1$ represents a $(C_1-C_6)$alkoxy radical, especially a methoxy radical, or an —$OSO_3^-$ radical, $R_2$ represents a $(C_1-C_6)$alkoxy radical or an —$OSO_3^-$ radical, $R_3$ represents a $(C_1-C_6)$alkoxy radical, especially a methoxy radical, or an —$OSO_3^-$ radical, or alternatively $R_3$ constitutes an —O—$CH_2$— bridge, the —$CH_2$— group being linked to the carbon atom bearing the carboxylic function on the same ring, Pe represents a saccharide sequence having the following formula:

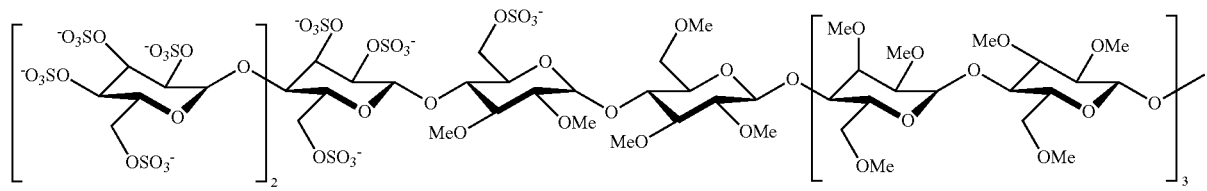
(Pe)

and the pharmaceutically acceptable salts thereof.

The polysaccharide parts consist of uncharged and/or partially charged and/or fully charged alkylated monosaccharide units. The charged or uncharged units may be dispersed along the entire length of the chain or, in contrast, they may be grouped in charged or uncharged saccharide domains.

In the present description, it has been chosen to represent the $^1C_4$ conformation for L-iduronic acid and the $^4C_1$ conformation for D-glucuronic acid, but it is well known that, in general, the conformation in solution of monosaccharide units fluctuates.

Thus, L-iduronic acid may be of $^4C_1$ $^2S_0$ or $^4C_1$ conformation.

The invention includes hexadecasaccharides in their acid form or in the form of any of their pharmaceutically acceptable salts. In the acid form, the —$COO^-$ and —$SO_3^-$ functions are in —COOH and —$SO_3H$ form, respectively.

The term "pharmaceutically acceptable salt of the polysaccharides of the invention" means a polysaccharide in which one or more of the $COO^-$ and/or —$SO_3^-$ functions are ionically bonded to a pharmaceutically acceptable cation. The salts that are preferred according to the invention are those whose cation is chosen from alkali metal cations and even more preferably those whose cation is $Na^+$ or $K^+$.

The compounds of formula I above also comprise those in which one or more hydrogen or carbon atoms have been replaced with the radioactive isotope thereof, for example tritium or $^{14}C$. Such labelled compounds are useful in research, metabolism or pharmacokinetic studies, in biochemical tests as ligands.

In the context of the present invention, the following definitions apply:

a $(C_1-C_6)$alkoxy radical: a radical —O-alkyl, the alkyl group being a linear or branched saturated aliphatic radical containing a chain of 1 to 6 carbon atoms. Examples of alkyl radicals that may be mentioned include methyl, ethyl, propyl, isopropyl, butyl, isobutyl and tert-butyl. Examples of $(C_1-C_6)$alkoxy radicals that may be mentioned include methoxy and ethoxy radicals, a "spacer" T: the sequences of formula $T_1$ or $T_2$ below:

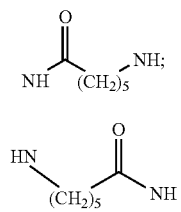
(T₁)

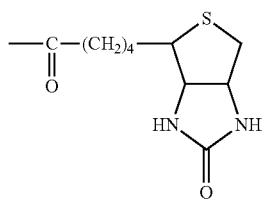
(T₂)

a biotinylated derivative:

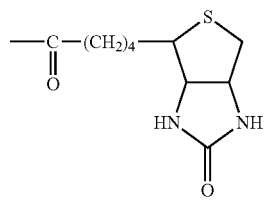

The biotin derivatives are commercially available ("Pierce" catalogue 1999-2000, pp. 62 to 81).

According to one of its preferred aspects, the present invention relates to the biotinylated hexadecasaccharides of general formula I in which:

R represents a methoxy radical, or an —OSO$_3^-$ radical,
R$_1$ represents a methoxy radical,
R$_2$ represents an —OSO$_3^-$ radical,
R$_3$ represents a methoxy radical.

According to another of its particularly preferred aspects, the invention relates to the following biotinylated hexadecasaccharides:

Methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-O-(2,3,6-tri-O-methyl-β-D-glucopyranosyl)-(1→4)]$_3$-(2-[N-(6-biotinamido hexanoyl)]-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-3-O-methyl-2,6-di-O-sulfonato-α-D-glucopyranoside, sodium salt Methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]$_3$-(2-[N-(6-biotinamido hexanoyl)]-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt In its principle, the process for preparing the compounds according to the invention uses di- or oligosaccharide base synthons prepared as reported previously in the literature. Reference will be made especially to the patents or patent applications EP 300 099, EP 529 715, EP 621 282 and EP 649 854 and also to the documents from C. van Boeckel and M. Petitou, *Angew. Chem. Int. Ed. Engl.*, (1993), 32, pp. 1671-1690. These synthons are then coupled to one another so as to give a fully protected equivalent of a polysaccharide according to the invention. This protected equivalent is then converted into a compound according to the invention.

One of the base synthons mentioned above contains a particular protected function allowing the subsequent introduction of biotin or of a biotin derivative, for example a latent amine function in the form of an azido group or protected in the form of N-phthalimido.

In the coupling reactions mentioned above, a "donor" di- or oligosaccharide, activated on its anomeric carbon, reacts with an "acceptor" di- or oligosaccharide containing a free hydroxyl.

The present invention relates to a process for preparing the compounds of formula I, characterized in that:

in a first step, a fully protected equivalent of the desired hexadecasaccharide of formula I is obtained, containing a protected pentasaccharide precursor, especially bearing a suitably protected amine function for the subsequent introduction of biotin or of a biotin derivative, this protected pentasaccharide precursor itself being extended by a protected precursor of the polysaccharide domain Pe;

in a second step, the negatively charged groups are introduced and/or demasked;

in a third step, the amine function is deprotected and the biotin or the biotin derivative is then introduced.

The pentasaccharide onto which will be grafted the biotin or the biotin derivative is synthesized according to the methods described in particular in the patent applications published under the numbers WO 98/03554 and WO 99/36443 and also in the literature (cited above).

The polysaccharide part that is the precursor of Pe is synthesized according to reactions that are well known to those skilled in the art, using the methods for the synthesis of oligosaccharides (G. J. Boons, *Tetrahedron*, (1996), 52, pp. 1095-1121, WO 98/03554 and WO 99/36443) or an oligosaccharide when an oligosaccharide that is a glycoside bond donor is coupled with an oligosaccharide that is a glycoside bond acceptor to give another oligosaccharide equal in size to the sum of the sizes of the two reactive species. This sequence is repeated until the compound of formula I is obtained. The nature and profile of the charge of the desired final compound determine the nature of the chemical species used in various steps of the synthesis, according to the rules that are well known to those skilled in the art. Reference may be made, for example, to C. van Boeckel and M. Petitou, *Angew. Chem. Int. Ed. Engl.*, (1993), 32, pp. 1671-1690 or to H. Paulsen, "Advances in selective chemical syntheses of complex oligosaccharides", *Angew. Chem. Int. Ed. Engl.*, (1982), 21, pp. 155-173.

The compounds of the invention are obtained from the fully protected polysaccharide precursors thereof by using the following sequence of reactions:

the alcohol functions that are to be converted into O-sulfo groups and the carboxylic acids are deprotected by removal of the protecting groups used during the preparation of the backbone, and then the sulfo groups are introduced next, the amine function that allows the introduction of biotin or the biotin derivative is deprotected, the biotin derivative is introduced via a standard amino/acid coupling reaction.

The compounds of the invention may naturally be prepared by using various strategies known to those skilled in the art of oligosaccharide synthesis.

The process described above is the preferred process of the invention. However, the compounds of formula I may be prepared via other well-known methods of sugar chemistry described, for example, in "Monosaccharides, Their chemistry and their roles in natural products", P. M. Collins and R. J. Ferrier, J. Wiley & Sons, (1995) and in G. J. Boons, *Tetrahedron*, (1996), 52, pp. 1095-1121.

The pentasaccharides Pe may thus be obtained from disaccharide synthons as described in the publication by C. van Boeckel and M. Petitou, *Angew. Chem. Int. Ed. Engl.*, (1993), 32, pp. 1671-1690.

The protecting groups used in the process for preparing the compounds of formula I are those commonly used in sugar chemistry, for example in "Protective Groups in Organic Synthesis", (1981), T. W. Greene, John Wiley & Sons, New York.

The protecting groups are advantageously chosen, for example, from acetyl, halomethyl, benzoyl, levulinyl, benzyl, substituted benzyl, optionally substituted trityl, tetrahydropyranyl, allyl, pentenyl, tert-butyldimethylsilyl (tBDMS) and trimethylsilylethyl groups.

The activating groups are those conventionally used in sugar chemistry according to, for example, G. J. Boons, *Tetrahedron*, (1996), 52, pp. 1095-1121. These activating groups are chosen, for example, from imidates, thioglycosides, pentenylglycosides, xanthates, phosphites and halides.

As regards both the way in which the biotin derivative is linked to the oligosaccharide and the nature of the biotin derivative, the chemical literature offers other possibilities that can possibly be used by means of sets of protecting groups that are well known to those skilled in the art. Use will preferably be made of an amine function, or a thiol function, or a carboxylic acid function or alternatively an aldehyde function, which will be reacted with a biotin derivative comprising a reactive group of the activated ester, maleimide, iodoacetyl or primary amine type, the reaction taking place according to the conditions described in the literature (Savage et al., "Avidin-Biotin Chemistry: A Handbook"; (1992), Pierce Chemical Company).

The process described above makes it possible to obtain the compounds of the invention in the form of salts. To obtain the corresponding acids, the compounds of the invention, in the form of salts, are placed in contact with a cation-exchange resin in acid form.

The compounds of the invention in acid form may then be neutralized with a base to obtain the desired salt. Any mineral or organic base that gives pharmaceutically acceptable salts with the compounds of formula I may be used for the preparation of the salts of the compounds of formula I. Sodium hydroxide, potassium hydroxide, calcium hydroxide or magnesium hydroxide is preferably used as base. The sodium and calcium salts of the compounds of formula I are the preferred salts.

The compounds according to the invention underwent biochemical and pharmacological studies.

1. Measurement of the Anti-factor IIa Activity and of the Anti-factor Xa Activity The circulating activity of the compounds according to the invention may be measured by means of their anti-factor IIa activity and the anti-factor Xa activity as described by Herbert et al., *Thromb Haemost.*, (2001), 85(5), pp. 852-60. The compounds according to the invention are administered intravenously (IV) or subcutaneously (SC) to rats. An IV injection of avidin results in a large decrease in the circulating concentration of compound according to the invention (greater than 70%).

For example, the circulating concentration of the compound according to Example 1, after IV injection of 100 nmol/kg, is reduced by 88% (reduction measured via the anti-factor Xa activity) and 91% (reduction measured via the anti-factor IIa activity) 2 minutes after the IV administration of avidin (10 mg/kg/625 nmol/kg).

The circulating concentration of the compound according to Example 2, after IV injection of 100 nmol/kg, is reduced by 76% (reduction measured via the anti-factor Xa activity) and 89% (reduction measured via the anti-factor IIa activity) 5 minutes after the IV administration of avidin (10 mg/kg/625 nmol/kg).

Equivalent inhibitions for the two activities are observed when the compounds according to Examples 1 and 2 are administered SC:

2. Measurement of the Global Antithrombotic Activity and Neutralization with Avidin The global antithrombotic activity of the compounds according to the invention and their neutralization was studied in a model of venous thrombosis consisting of an injection of tissue factor followed by stasis of rat vena cava, as described by Herbert et al., *Blood*, (1998), 91, pp. 4197-4205.

a) Measurement of the Global Antithrombotic Activity

The compounds of the present invention are powerful thrombosis inhibitors ($IC_{50}$ values of less than 50 nM).

For example, Examples 1 and 2 show $IC_{50}$ values in this model of 3 and 9.9 nM, respectively, after their IV administration.

For example, inhibition of the weight of the thrombus due to the compound according to Example 1 (at a concentration of 30 nmol/kg) is brought back to the control level by an IV injection of 3 mg/kg/208 nmol/kg of avidin.

b) Neutralization with Avidin: Bleeding Test in Rats

The effect of compounds according to the invention was evaluated in the bleeding test in rats (Herbert et al., *Blood*, (1998), 91, pp. 4197-4205). These compounds show high anticoagulant activity and thus increase the bleeding time in the animal models. Avidin neutralizes the effect of the compounds according to the invention on bleeding.

For example, the bleeding time induced in rats by 30 nmol/kg of the compound according to Example 1 is brought back to the control level by an IV administration of avidin (3 mg/kg; 208 nmol/kg).

For example, the bleeding time induced in rats by 100 nmol/kg of the compound according to Example 2 is brought back to the control level by an IV administration of avidin (10 mg/kg; 625 nmol/kg).

Thus, a subject of the present invention is also a process using avidin or streptavidin, characterized in that it allows the polysaccharides according to the invention to be neutralized. Avidin or streptavidin may be used for the preparation of medicaments for neutralizing the polysaccharides according to the present invention.

By virtue of their biochemical and pharmaceutical activity, the oligosaccharides of the present invention constitute highly advantageous medicaments. Their toxicity is entirely compatible with this use. They are also very stable and are thus particularly suitable for constituting the active principle of pharmaceutical specialties.

They can be used in various pathologies consecutive to a modification in the homeostasis of the clotting system appearing in particular during disorders of the cardiovascular and cerebrovascular system, for instance thromboembolic disorders associated with atherosclerosis and diabetes, such as unstable angina, apoplexy, post-angioplasty restenosis, endarterectomy or the insertion of endovascular prostheses; or thromboembolic disorders associated with post-thrombolysis rethrombosis, infarction, dementia of ischaemic origin, peripheral arterial diseases, blood dialysis, auricular fibrillations, or alternatively during the use of vascular prostheses for aorto-coronary bypasses. These products may moreover be used for the treatment or prevention of thromboembolic pathologies of venous origin, such as pulmonary embolisms. They may be used for preventing or treating the thrombotic complications observed, for example, following surgical operations, the growth of tumours or disruption of clotting, induced by bacterial, viral or enzymatic activators. In the case of their use during the insertion of prostheses, the compounds of the present invention can cover prostheses and thus make them haemocompatible. In particular, they can be attached to intravascular prostheses (stents). In this case, they can optionally be chemically modified by introduction of a suitable arm at the non-reducing or reducing end, as described according to EP 649 854.

The compounds of the present invention may also be used as adjuvants during endarterectomy performed with porous balloons.

The compounds according to the invention may be used for the preparation of medicinal products for treating the above diseases.

According to another of its aspects, a subject of the present invention is thus a pharmaceutical composition containing, as active principle, a synthetic polysaccharide according to the invention or a pharmaceutically acceptable salt thereof, optionally in combination with one or more inert and suitable excipients.

The said excipients are chosen according to the desired pharmaceutical form and the desired mode of administration: oral, sublingual, subcutaneous, intramuscular, intravenous, transdermal, transmucous, local or rectal.

The active principle may also be presented in the form of a complex with a cyclodextrin, for example α, β or γ-cyclodextrin, 2-hydroxypropyl-β-cyclodextrin or methyl-β-cyclodextrin.

The active principle may also be released by means of a balloon containing it or by means of an endovascular extender introduced into the blood vessels. The pharmacological efficacy of the active principle is thus unaffected.

In each dosage unit, the active principle is present in the amounts suited to the daily doses envisaged in order to obtain the desired prophylactic or therapeutic effect. Each dosage unit can contain from 0.1 to 100 mg and preferably 0.5 to 50 mg of active principle. These doses of anticoagulant compounds may be neutralized with doses of avidin or of streptavidin ranging from 1 to 1000 mg by intravenous injection, bolus or infusion.

The compounds according to the invention may also be used in combination with one or more other active principles that are useful for the desired therapy, for instance antithrombotic agents, anticoagulants, platelet aggregation inhibitors, for instance dipyridamole, aspirin, ticlopidine, clopidogrel or glycoprotein IIb/IIIa complex antagonists.

The methods, preparations and schemes below illustrate the synthesis of the various intermediates that are useful for obtaining the polysaccharides according to the invention. The examples of synthesis of hexadecasaccharides that follow illustrate the invention without limiting it.

| The following abbreviations are used: | |
|---|---|
| Bn: | benzyl; |
| Bz: | benzoyl; |
| Lev: | levulinyl; |
| Et: | ethyl; |
| Ph: | phenyl; |
| Me: | methyl; |
| Ac: | acetyl; |
| SEt: | thioethyl; |
| MP: | p-methoxyphenyl; |
| Biotin: | Hexahydro-2-oxo-1H-thieno[3,4-d]imidazole-4-pentanoic acid; |
| ESI: | Electron Spray Ionization; |
| TLC: | thin-layer chromatography; |
| m.p.: | melting point; |
| $[\alpha_D]$ = | optical rotation; |
| C = | concentration |
| Rf = | retention time measured on the TLC relative to the migration solvent front. |

The preparations and synthetic examples of the compounds of the invention are detailed for illustrative purposes in the text hereinbelow.

PREPARATIONS

SCHEME 1-Synthesis of monosaccharide 4

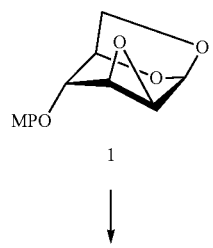

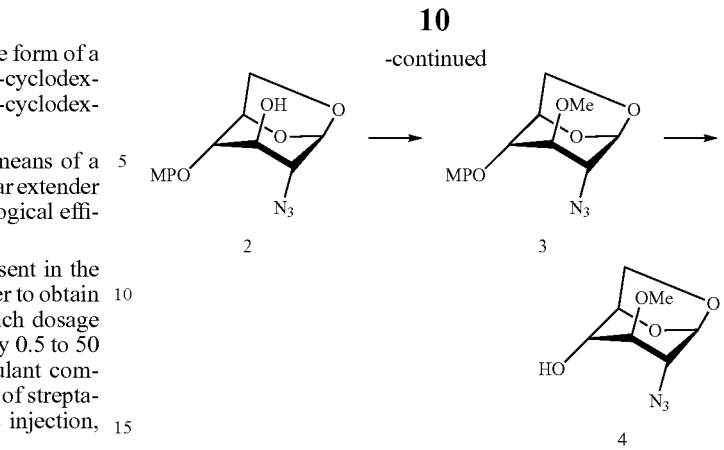

Preparation 1

Preparation of 1,6-anhydro-2-azido-2-deoxy-4-O-p-meth-oxyphenyl-β-D-glucopyranose (No. 2)

The compound 1,6:2,3-dianhydro-4-O-p-methoxy-phenyl-β-D-mannopyranose, No. 1, (4.39 g, 17.5 mmol) is synthesized by analogy with the method described in Brill and Tirefort, *Tetrahedron Lett.* (1998), 39, pp. 787-790. Compound 1 is dissolved in 130 ml of an N,N-dimethylformamide/water mixture [4/1 (v/v)] and sodium azide (22.8 g, 350 mmol) is then added. The reaction medium is heated at 120° C. for 6 hours. After filtering through Celite, the filtrate is diluted with ethyl acetate and then washed with water. The organic phase is dried over sodium sulfate, filtered and then concentrated under vacuum. The residue is recrystallized from an ethyl acetate/cyclohexane mixture (20 ml/7 ml) to give 4.46 g of compound 2 in the form of crystals.

m.p.: 144° C.

Preparation 2

Preparation of 1,6-anhydro-2-azido-2-deoxy-4-O-p-meth-oxyphenyl-3-O-methyl-β-D-glucopyranose (No. 3)

To a cooled (0° C.) mixture of compound 2 (4.08 g, 13.9 mmol) and methyl iodide (1.1 ml, 15.3 mmol) in anhydrous N,N-dimethylformamide (40 ml) is added portionwise sodium hydroxide (1.04 g) under an argon atmosphere. The mixture is stirred for 20 hours at room temperature. The excess sodium hydride is destroyed with methanol. After evaporating off the N,N-dimethylformamide, the residue is taken up in dichloromethane. The organic phase is washed with water, dried over sodium sulfate, filtered and then concentrated under vacuum. The residue is purified by chromatography on a column of silica gel [12/1 (v/v) toluene/ethyl acetate] to give 3.57 g of compound 3 in the form of a white solid.

m.p.: 68° C.

Preparation 3

Preparation of 1,6-anhydro-2-azido-2-deoxy-3-O-methyl-β-D-glucopyranose (No. 4)

A solution of compound 3 (8.0 g, 26.03 mmol) in 130 ml of an acetonitrile/water mixture [9/1 (v/v)] is added dropwise to a solution of cerium ammonium nitrate (86 g, 156.2 mmol) in 390 ml of an acetonitrile/water mixture [9/1 (v/v)]. The mixture is stirred at room temperature for 40 minutes and then diluted with ethyl acetate. The reaction mixture is dried over anhydrous sodium sulfate, filtered and concentrated. Filtration on silica gel allows the cerium ammonium nitrate residues to be partially removed. To purify the compound, an acetylation followed by a deacetylation are performed. The residue is taken up in dichloromethane (90 ml), and triethylamine (5.3 ml), dimethylaminopyridine (280 mg) and finally acetic anhydride (3.2 ml) are successively added. After 16 hours, the reaction medium is diluted with dichloromethane (250 ml). The organic phase is washed with 10% potassium hydrogen sulfate solution, with water, with 10% sodium hydrogen carbonate solution and then with water. The organic phase is then dried over anhydrous sodium sulfate, filtered and then concentrated under vacuum. The residue is purified by chromatography on a column of silica gel [10/1 (v/v) toluene/ethyl acetate] to give 4.9 g of the product in solid form. This solid is dissolved in 80 ml of a dichloromethane/methanol mixture [1/1 (v/v)] and sodium methoxide (544 mg) is then added. The mixture is stirred for 35 minutes and then neutralized with a Dowex® 50WX4 H⁺ resin, filtered and concentrated under vacuum. The residue is purified by chromatography on a column of silica gel [3/2 (v/v) toluene/ethyl acetate] to give 3.9 g of compound 4.

$[\alpha]_D = -27°$ (C=1.06, in dichloromethane).

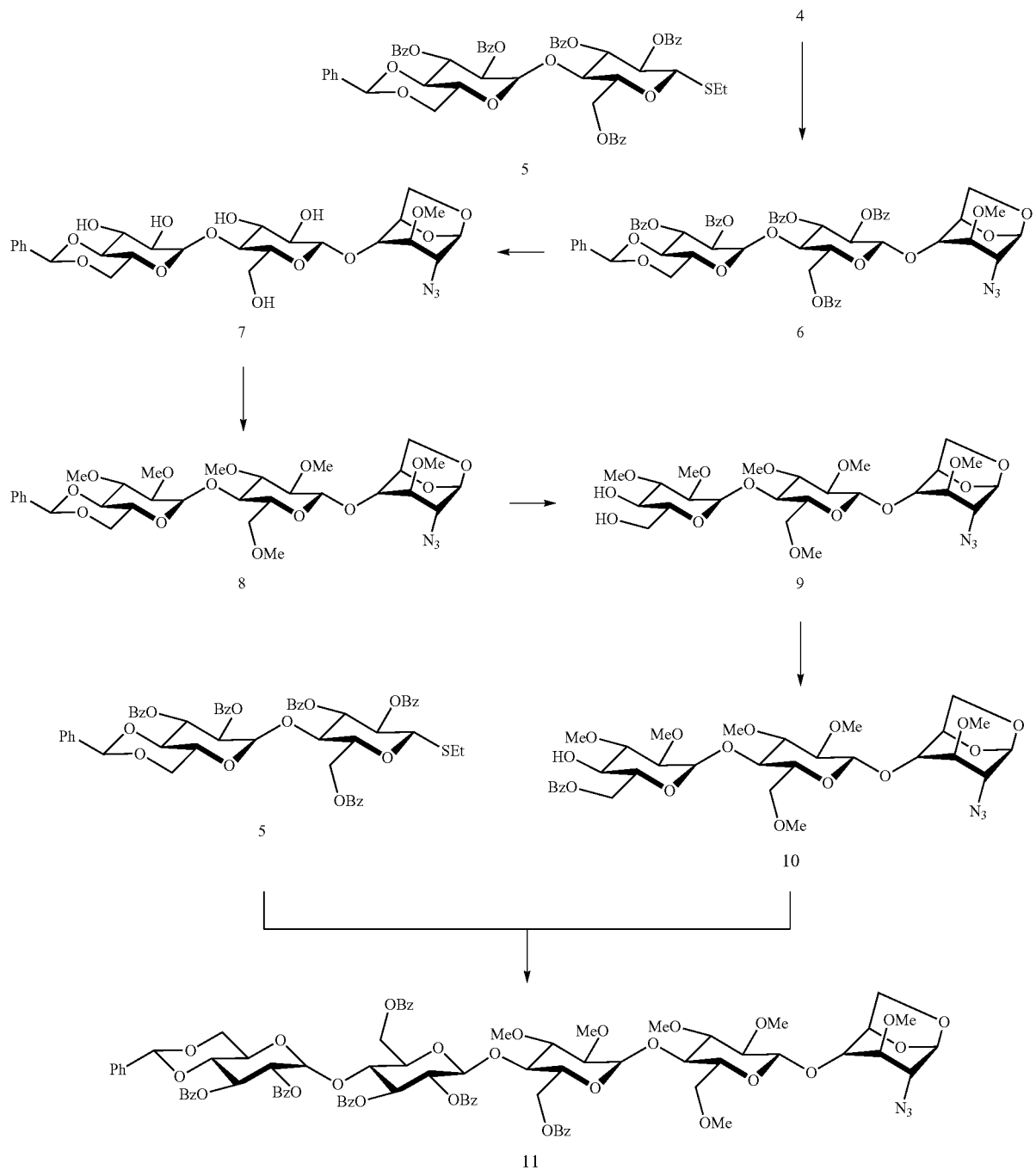

SCHEME 2 - Synthesis of the pentasaccharide 11

Preparation 4

Preparation of (2,3-di-O-benzoyl-4,6-O-benzylidene-α-D-glucopyranosyl)-(1→4)-(2,3,6-tri-O-benzoyl-β-D-glucopyranosyl)-(1→4)-1,6-anhydro-2-azido-2-deoxy-3-O-methyl-β-D-glucopyranose (No. 6)

A mixture of the thioglycoside compound 5 (9.00 g, 9.04 mmol), obtained by analogy with Preparation 1 described in the patent application published under the number WO 99/36443, compound 4 obtained in Preparation 3 (1.65 g, 8.22 mmol) and powdered 4 Å molecular sieves (9.05 g) in toluene (180 ml) is stirred under an argon atmosphere for 1 hour. The mixture is then cooled to −20° C. A solution of N-iodosuccinimide (2.14 g, 9.5 mmol) and trifluoromethanesulfonic acid (96 µl, 1.09 mmol) in 47 ml of a dichloromethane/dioxane mixture [1/1 (v/v)] is added dropwise to the reaction mixture. After 10 minutes, the reaction mixture is filtered through Celite, diluted with dichloromethane (1000 ml) and washed successively with 1M sodium thiosulfate solution, 10% sodium hydrogen carbonate solution and water. The reaction mixture is then dried over anhydrous sodium sulfate and then concentrated under vacuum. Purification of the residue is performed by chromatography on a column of silica gel [5/1 (v/v) toluene/ethyl acetate] to give 9.20 g of the trisaccharide 6.

$[\alpha]_D$=+44° (C=1.30, in dichloromethane).

Preparation 5

Preparation of (4,6-O-benzylidene-α-D-glucopyranosyl)-(1→4)-(β-D-glucopyranosyl)-(1→4)-1,6-anhydro-2-azido-2-deoxy-3-O-methyl-β-D-glucopyranose (No. 7)

To a solution of compound 6 (9.2 g, 8.11 mmol) in dioxane (81 ml) is added potassium tert-butoxide (1.82 g, 16.2 mmol). The mixture is stirred for 3 hours and then neutralized with a Dowex® 50WX4 H⁺ resin, filtered and concentrated under vacuum. After chromatography on a column of silica gel [8/1 (v/v) dichloromethane/methanol], 5.46 g of compound 7 are isolated in the form of a foam.

TLC on silica gel, dichloromethane/methanol [9/1 (v/v)]: Rf=0.35

$[\alpha]_D$=+38° (C=0.84 in dichloromethane).

Preparation 6

Preparation of (4,6-O-benzylidene-2,3-di-O-methyl-α-D-glucopyranosyl)-(1→4)-(2,3,6-tri-O-methyl-β-D-glucopyranosyl)-(1→4)-1,6-anhydro-2-azido-2-deoxy-3-O-methyl-β-D-glucopyranose (No. 8)

To a cooled (0° C.) mixture of compound 7 (5.05 g, 8.23 mmol) and methyl iodide (3.8 ml, 61.7 mmol) in anhydrous N,N-dimethylformamide (150 ml) is added portionwise sodium hydroxide (1.73 g, 72.0 mmol) under an argon atmosphere. The mixture is stirred for 20 hours at room temperature. The excess sodium hydride is destroyed with methanol (8 ml) and the reaction mixture is poured into ice-cold water (400 ml). After extraction with ethyl acetate, the organic phase is washed with saturated sodium chloride solution, dried over anhydrous sodium sulfate and then concentrated under vacuum. The residue is purified by chromatography on a column of silica gel [7/1 and then 5/1 (v/v) dichloromethane/acetone] to give 4.8 g of compound 8.

$[\alpha]_D$=+49° (C=1.02, in dichloromethane).

TLC on silica gel, dichloromethane/acetone [5/1 (v/v)]: Rf=0.45

Preparation 7

Preparation of (2,3-di-O-methyl-α-D-glucopyranosyl)-(1→4)-(2,3,6-tri-O-methyl-β-D-glucopyranosyl)-(1→4)-1,6-anhydro-2-azido-2-deoxy-3-O-methyl-β-D-glucopyranose (No. 9)

Compound 8 (5.3 g, 7.75 mmol) is dissolved in 60% acetic acid (233 ml) and stirred for 1 hour 30 minutes at 80° C. The mixture is concentrated and co-evaporated with toluene. The residue is purified by chromatography on a column of silica gel [4/1 (v/v) toluene/ethanol] to give 5.09 g of compound 9.

$[\alpha]_D$=+57° (C=1.06 in dichloromethane).

TLC on silica gel, toluene/ethanol [4/1 (v/v)]: Rf=0.36

Preparation 8

Preparation of (6-O-benzoyl-2,3-di-O-methyl-α-D-glucopyranosyl)-(1→4)-(2,3,6-tri-O-methyl-β-D-glucopyranosyl)-(1→4)-1,6-anhydro-2-azido-2-deoxy-3-O-methyl-β-D-glucopyranose (No. 10)

To a solution of compound 9 (5.09 g, 8.55 mmol) in dichloromethane (85 ml) are added 1-benzyloxy-1H-benzotriazole (2.86 g, 11.97 mmol) and triethylamine (1.80 ml). The mixture is stirred for 20 hours at room temperature and then diluted with dichloromethane. The organic phase is washed with saturated sodium hydrogen carbonate solution and then with water. The organic phase is then dried over anhydrous sodium sulfate, filtered and then concentrated under vacuum. The residue is purified by chromatography on a column of silica gel [15/2 (v/v) toluene/ethanol] to give 4.85 g of compound 10.

$[\alpha]_D$=+43° (C=1.06, in dichloromethane).

TLC on silica gel, toluene/ethanol [15/2 (v/v)]: Rf=0.31

Preparation 9

Preparation of (2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 11)

The coupling reaction of compound 10 (4.38 g, 6.26 mmol) with compound 5 ("glycosyl donor deleted"), obtained by analogy with Preparation 1 described in the patent application published under the number WO 99/36443 (11.85 g, 11.9 mmol) is performed according to the procedure described in Preparation 4, to give 8.39 g of compound 11.

$[\alpha]_D$=+61° (C=1.06, in dichloromethane).

SCHEME 3 - Synthesis of the pentasaccharide 15

11

↓

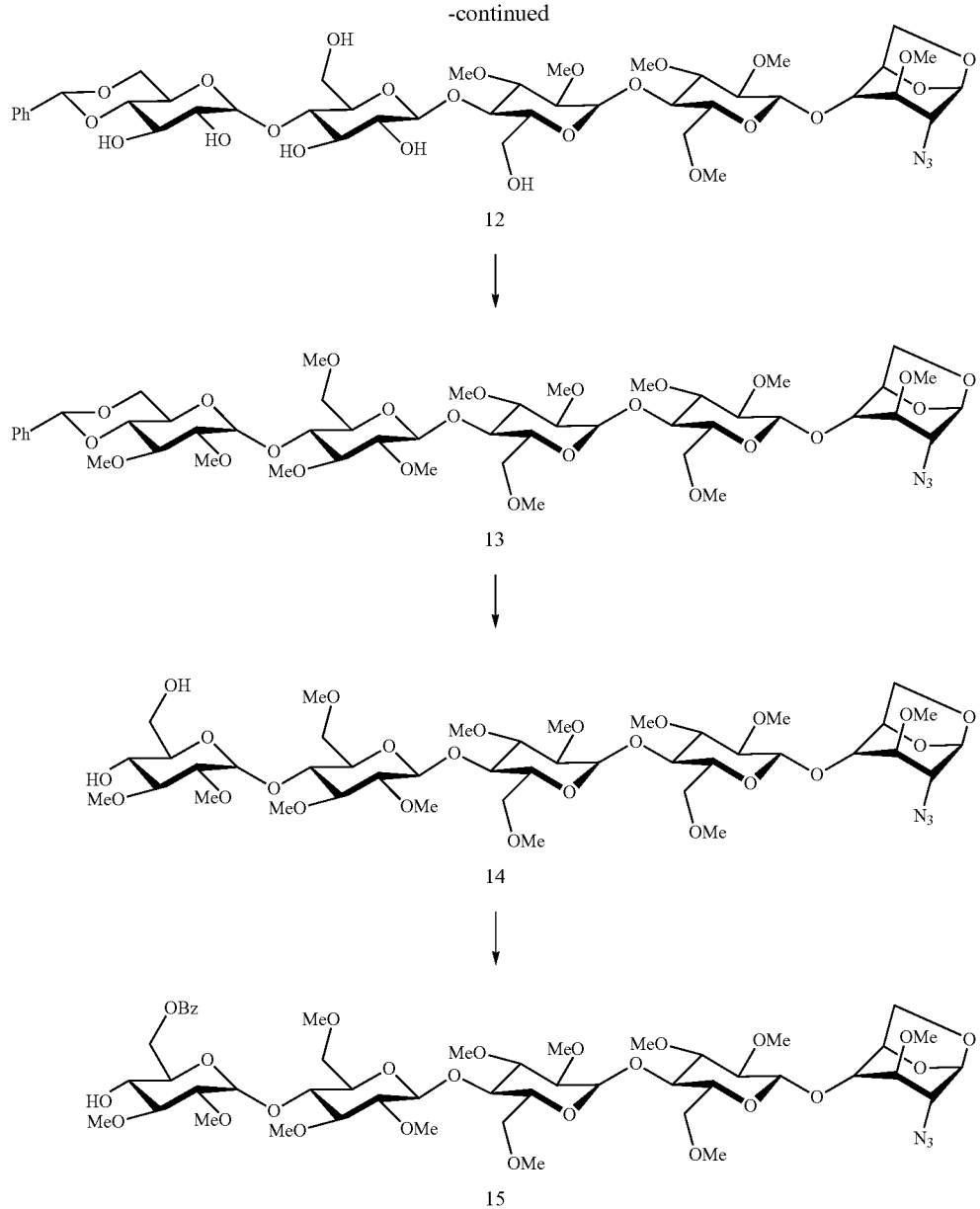

Preparation 10

Preparation of (4,6-O-benzylidene-α-D-glucopyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 12)

Compound 11 (8.36 g, 5.12 mmol), obtained in Preparation 9, is converted into compound 12 according to the same procedure as that described for Preparation 5. After chromatography on a column of silica gel, compound 12 (4.92 g) is obtained in the form of a glass.

TLC on silica gel, dichloromethane/methanol [10/1 (v/v)]: Rf=0.41

Preparation 11

Preparation of (4,6-O-benzylidene-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 13)

Compound 12 (4.57 g, 4.54 mmol) is converted into compound 13 according to the same procedure as that described for Preparation 6. The crude product is purified by chromatography on a column of silica gel to give 4.94 g of compound 13.

$[\alpha]_D$=+68° (C=0.93, in dichloromethane).

TLC on silica gel, toluene/ethanol [8/1 (v/v)]: Rf=0.39

Preparation 12

Preparation of (2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 14)

Compound 13 (4.89 g, 4.48 mmol) is converted into compound 14 according to the same procedure as that described for Preparation 7. The crude product is purified by chromatography on a column of silica gel to give 4.30 g of compound 14.
$[\alpha]_D$=+80° (C=1.05, in dichloromethane).
TLC on silica gel, toluene/ethanol [4/1 (v/v)]: Rf=0.31

Preparation 13

Preparation of (6-O-benzoyl-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 15)

Compound 14 (4.26 g, 4.25 mmol) is converted into compound 15 according to the same procedure as that described for Preparation 8. The crude product is purified by chromatography on a column of silica gel to give 4.33 g of compound 15.
$[\alpha]_D$=+59° (C=1.0, in dichloromethane).
TLC on silica gel, toluene/acetone [4/3 (v/v)]: Rf=0.38

SCHEME 4 - Synthesis of the heptasaccharide 20

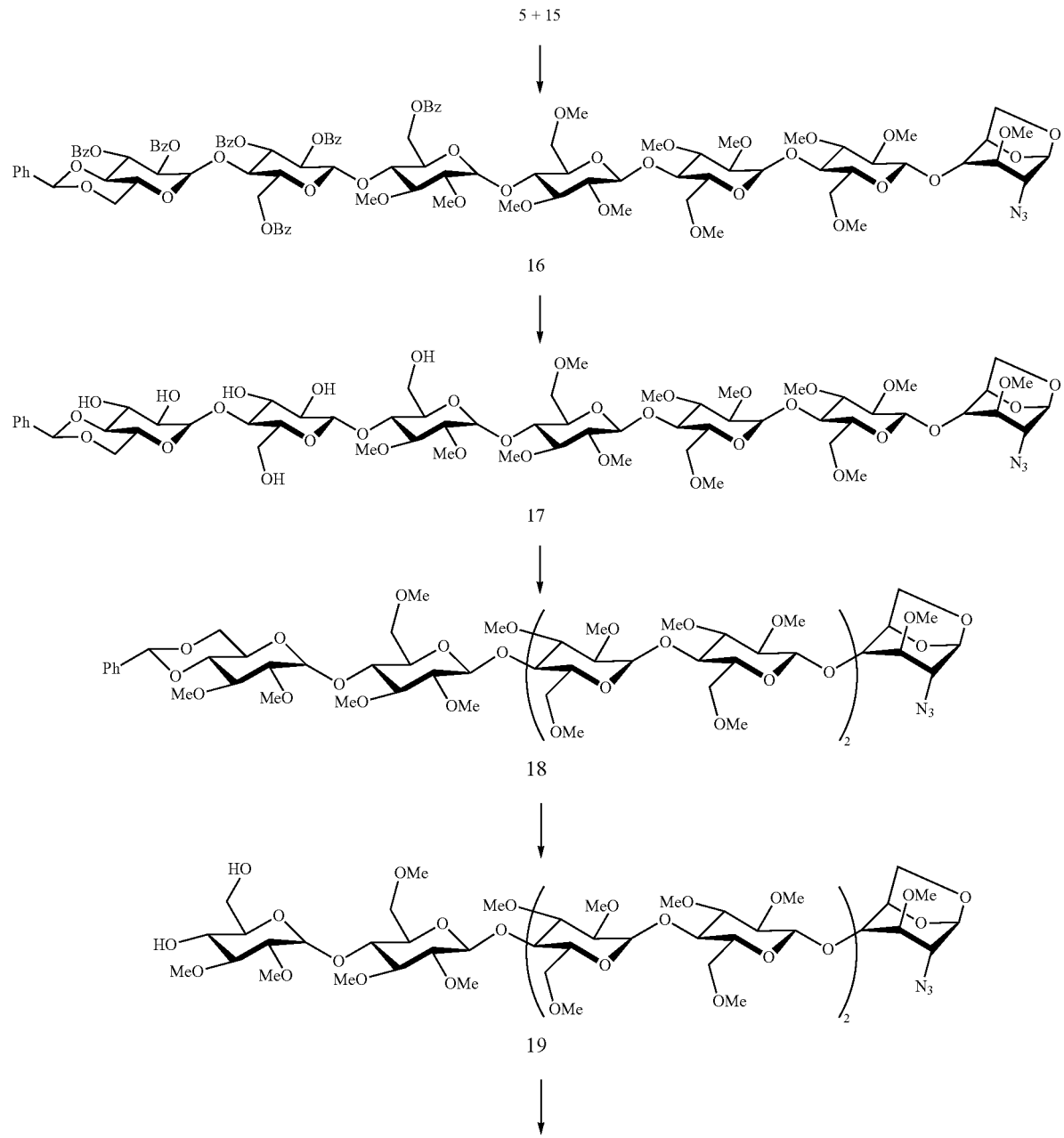

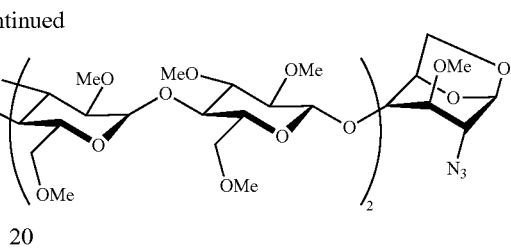

-continued

20

Preparation 14

Preparation of (2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 16)

The coupling reaction of the thioglycoside 5 (4.90 g, 4.93 mmol), obtained by analogy with the preparation described in the patent application published under the number WO 99/36443, and of compound 15 (4.55 g, 4.11 mmol), described in Preparation 13, is performed according to the procedure described in Preparation 4. The residue obtained after extraction is purified by chromatography on a column of silica gel to give 8.07 g of compound 16.

$[\alpha]_D = +71°$ (C=0.99, in dichloromethane).

Preparation 15

Preparation of (4,6-O-benzylidene-α-D-glucopyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-(2,3,6-tri-O-methyl-α-D-glucopyranosyl)-(1→4)-(2,3,6-tri-O-methyl-β-D-glucopyranosyl)-1,6-anhydro-2-azido-2-deoxy-3-O-methyl-β-D-glucopyranose (No. 17)

Compound 16 is converted into compound 17 according to the procedure described in Preparation 5.
TLC on silica gel, dichloromethane/methanol [8/1 (v/v)]: Rf=0.45

Preparation 16

Preparation of (4,6-O-benzylidene-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₂-1,6-anhydro-2-azido-2-deoxy-3-O-methyl-β-D-glucopyranose (No. 18)

Compound 17 is converted into compound 18 according to the procedure described in Preparation 6.
TLC on silica gel, toluene/acetone [5/4 (v/v)]: Rf=0.40

Preparation 17

Preparation of (2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₂-1,6-anhydro-2-azido-2-deoxy-3-O-methyl-β-D-glucopyranose (No. 19)

Compound 18 is converted into compound 19 according to the procedure described in Preparation 7.
TLC on silica gel, dichloromethane/methanol [10/1 (v/v)]: Rf=0.41

Preparation 18

Preparation of (6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₂-1,6-anhydro-2-azido-2-deoxy-3-O-methyl-β-D-glucopyranose (No. 20)

Compound 19 is converted into compound 20 according to the procedure described in Preparation 8.
TLC on silica gel, cyclohexane/acetone [1/1 (v/v)]: Rf=0.36

SCHEME 5 - Synthesis of the nonasaccharide 25

5 + 20

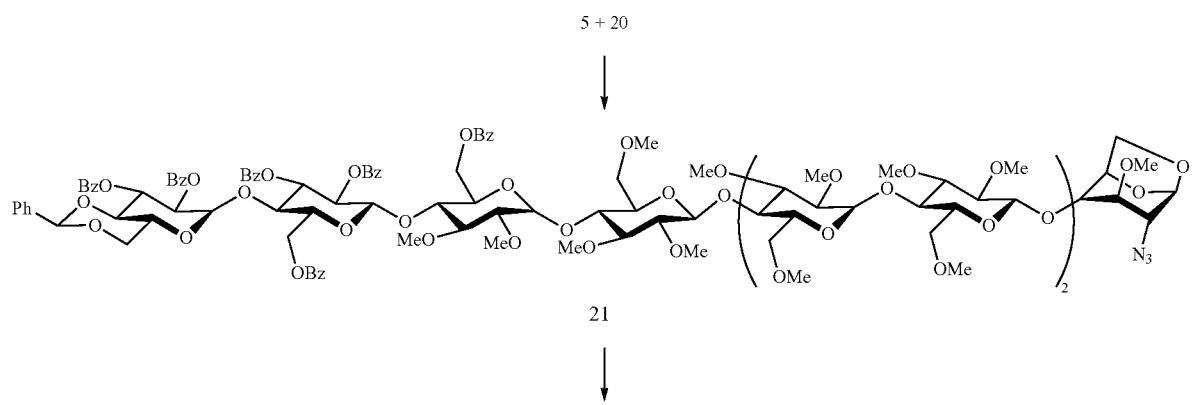

21

-continued

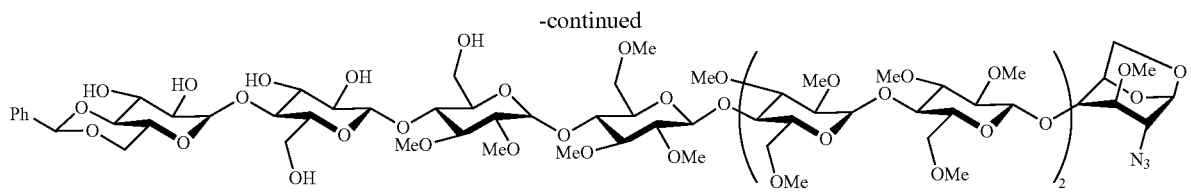

22

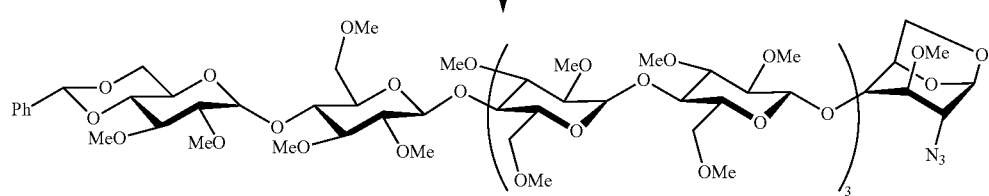

23

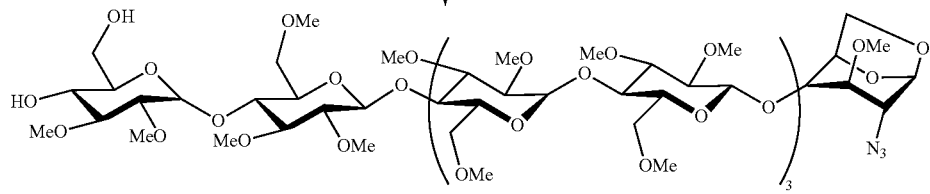

24

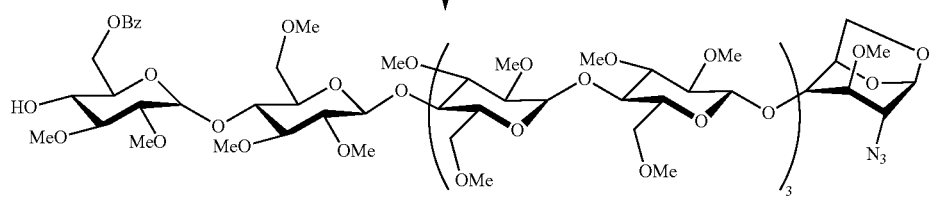

25

Preparation 19

Preparation of (2,3-di-O-benzoyl-4,6-O-benzylidene-α-D-glucopyranosyl)-(1→4)-(2,3,6-tri-O-benzoyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)]$_2$-(1→4)-1,6-anhydro-2-azido-2-deoxy-3-O-methyl-β-D-glucopyranose (No. 21)

The coupling reaction of the thioglycoside 5 (3.91 g, 3.93 mmol), obtained by analogy with Preparation 1 described in the patent application published under the number WO 99/36443, and of compound 20 (4.97 g, 3.27 mmol), obtained in Preparation 18, is performed according to the procedure described in Preparation 4. The crude product is purified by chromatography on a column of silica gel to give 8.06 g of compound 21.

$[\alpha]_D$=+77° (C=0.92, in dichloromethane)

Preparation 20

Preparation of (4,6-O-benzylidene-α-D-glucopyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)]$_2$-(1→4)-1,6-anhydro-2-azido-2-deoxy-3-O-methyl-β-D-glucopyranose (No. 22)

Compound 21 is converted into compound 22 according to the procedure described in Preparation 5.

TLC on silica gel, dichloromethane/methanol [9/1 (v/v)]: Rf=0.34

Preparation 21

Preparation of (4,6-O-benzylidene-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)]$_3$-(1→4)-1,6-anhydro-2-azido-2-deoxy-3-O-methyl-β-D-glucopyranose (No. 23)

Compound 22 is converted into compound 23 according to the procedure described in Preparation 6.
TLC on silica gel, cyclohexane/acetone [1/1 (v/v)]: Rf=0.44

Preparation 22

Preparation of (2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)]$_3$-(1→4)-1,6-anhydro-2-azido-2-deoxy-3-O-methyl-β-D-glucopyranose (No. 24)

Compound 23 is converted into compound 24 according to the procedure described in Preparation 7.

TLC on silica gel, dichloromethane/methanol [10/1 (v/v)]: Rf=0.43

Preparation 23

Preparation of (6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)]$_3$-(1→4)-1,6-anhydro-2-azido-2-deoxy-3-O-methyl-β-D-glucopyranose (No. 25)

Compound 24 is converted into compound 25 according to the procedure described in Preparation 8.

TLC on silica gel, dichloromethane/methanol [10/1 (v/v)]: Rf=0.64

SCHEME 6 - Synthesis of the dodecasaccharide 30

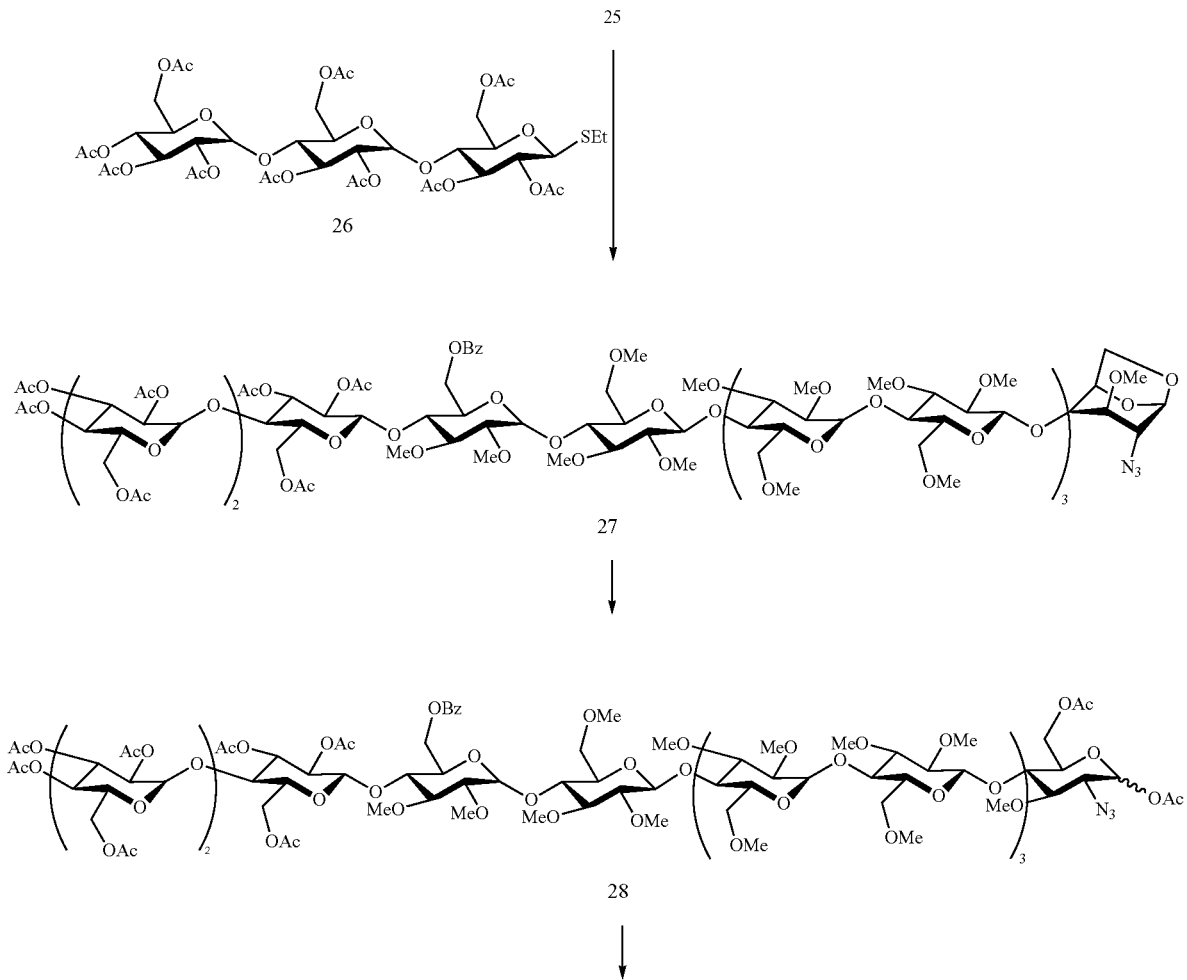

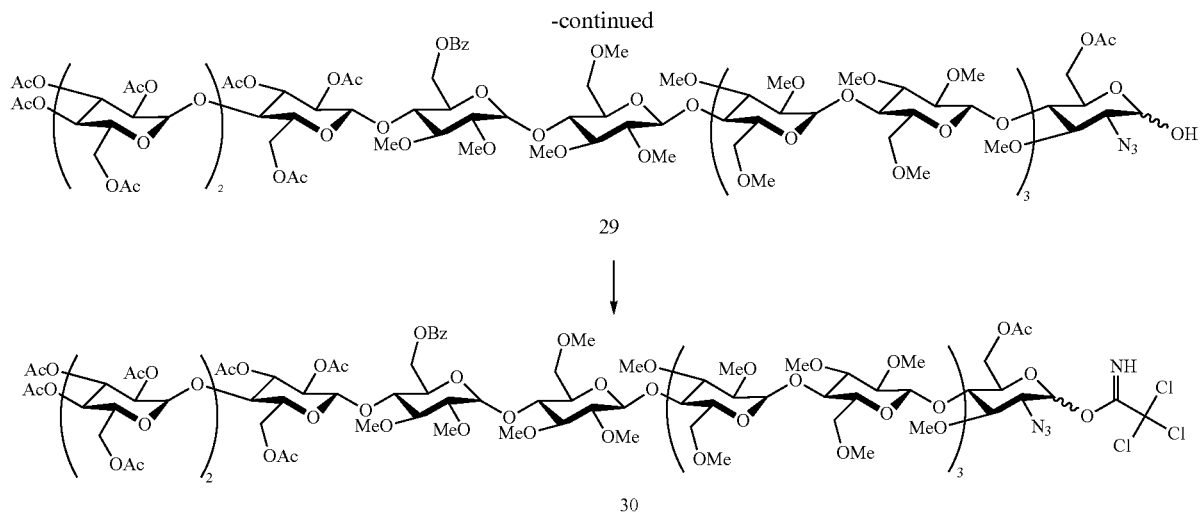

Preparation 24

Preparation of (2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-1,6-anhydro-2-azido-2-deoxy-3-O-methyl-β-D-glucopyranose (No. 27)

A mixture of the thioglycoside compound 26 (10.1 g, 10.4 mmol), prepared by analogy with the method described in Preparation 36 of the patent application published under the number WO 99/36443, of the acceptor compound 25 (5.02 g, 2.61 mmol) obtained in Preparation 23 and of powdered 4 Å molecular sieves (14.5 g) in toluene (220 ml) is stirred under an argon atmosphere for 1 hour. The reaction mixture is cooled to 0° C. and a solution of N-iodosuccinimide (2.58 g) and trifluoromethanesulfonic acid (366 μl) in 57 ml of a dichloromethane/dioxane mixture [1/1 (v/v)] is introduced therein. After 40 minutes, the mixture is filtered through Celite, diluted with toluene and successively washed with 1M sodium thiosulfate solution, 10% sodium hydrogen carbonate solution and water. The reaction mixture is then dried over anhydrous sodium sulfate, filtered and then concentrated under vacuum. The residue is purified by chromatography on a column of silica gel [17/1/1 and then 14/1/1 (v/v/v) dichloromethane/ethyl acetate/ethanol] to give 5.87 g of compound 27.

TLC on silica gel, dichloromethane/ethyl acetate/ethanol [8/0.5/0.5 (v/v/v)]; [toluene/acetone (1/1 (v/v)]: Rf=0.41

Preparation 25

Preparation of (2,3,4,6-tetra-O-acetyl-α-D-glucopyranosyl)-(1→4)-(2,3,6-tri-O-acetyl-α-D-glucopyranosyl)(1→4)-(2,3,6-tri-O-acetyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-1,6-di-O-acetyl-2-azido-2-deoxy-3-O-methyl-D-glucopyranose (No. 28)

A solution of compound 27 (4.06 g, 1.44 mmol) in a mixture of acetic anhydride (13.6 ml) and trifluoroacetic acid (1.2 ml) is stirred for 6 hours. After concentrating, the mixture is co-evaporated with toluene (5×25 ml). The residue is purified by chromatography on a column of silica gel [3/1/1 (v/v/v) cyclohexane/ethyl acetate/ethanol] to give 2.930 g of compound 28.

TLC on silica gel, toluene/acetone [1/1 (v/v)]: Rf=0.44

Preparation 26

Preparation of (2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)-(2,3,6-tri-O-methyl-β-D-glucopyranosyl)-(1→4)]₃-6-O-acetyl-2-azido-2-deoxy-3-O-methyl-D-glucopyranose (No. 29)

A solution of compound 28 (2.72 g, 0.928 mmol) and of benzylamine (3.9 ml, 35.2 mmol) in tetrahydrofuran is stirred at room temperature for 16 hours. The reaction mixture is diluted with ethyl acetate, washed with 1M hydrochloric acid and with water, dried over sodium sulfate, filtered and then concentrated under vacuum. Purification of the residue by chromatography on a column of silica gel [4/5 (v/v) cyclohexane/acetone] gives 2.21 g of compound 29.

TLC on silica gel, cyclohexane/acetone [4/5 (v/v)]: Rf=0.42

Preparation 27

Preparation of (2,3,4,6-tetra-O-acetyl-α-D-glucopyranosyl)-(1→4)-(2,3,6-tri-O-acetyl-α-D-glucopyranosyl)-(1-+4)-(2,3,6-tri-O-acetyl-β-D-glucopyranosyl)-(1→4)-(6-O-benzoyl-2,3-di-O-methyl-α-D-glucopyranosyl)-(1-+4)-(2,3,6-tri-O-methyl-β-D-glucopyranosyl)-(1→4)-[(2,3,6-tri-O-methyl-α-D-glucopyranosyl)-(1-4.4)-(2,3,6-tri-O-methyl-β-D-glucopyranosyl)-(1→4)]₃-6-O-acetyl-2-azido-2-deoxy-3-O-methyl-D-glucopyranose trichloroacetimidate (No. 30)

Trichloroacetonitrile (54.6 μl, 541 μmol) and caesium carbonate (56.4 mg, 173 μmol) are added to a solution of compound 29 (0.313 g, 108 μmol) in dichloromethane (3 ml). After stirring for 1 hour 30 minutes, the mixture is filtered and then concentrated. The residue is purified by chromatography on a column of silica gel, using for the elution a mixture of cyclohexane/ethyl acetate/ethanol [2/0.5/0.5 (v/v/v)] containing 0.1% triethylamine, to give 245 mg of compound 30.

TLC on silica gel, cyclohexane/ethyl acetate/ethanol [5/1.5/1.5 (v/v/v)]: Rf=0.41

SCHEME 7 - Synthesis of the tetrasaccharide 34

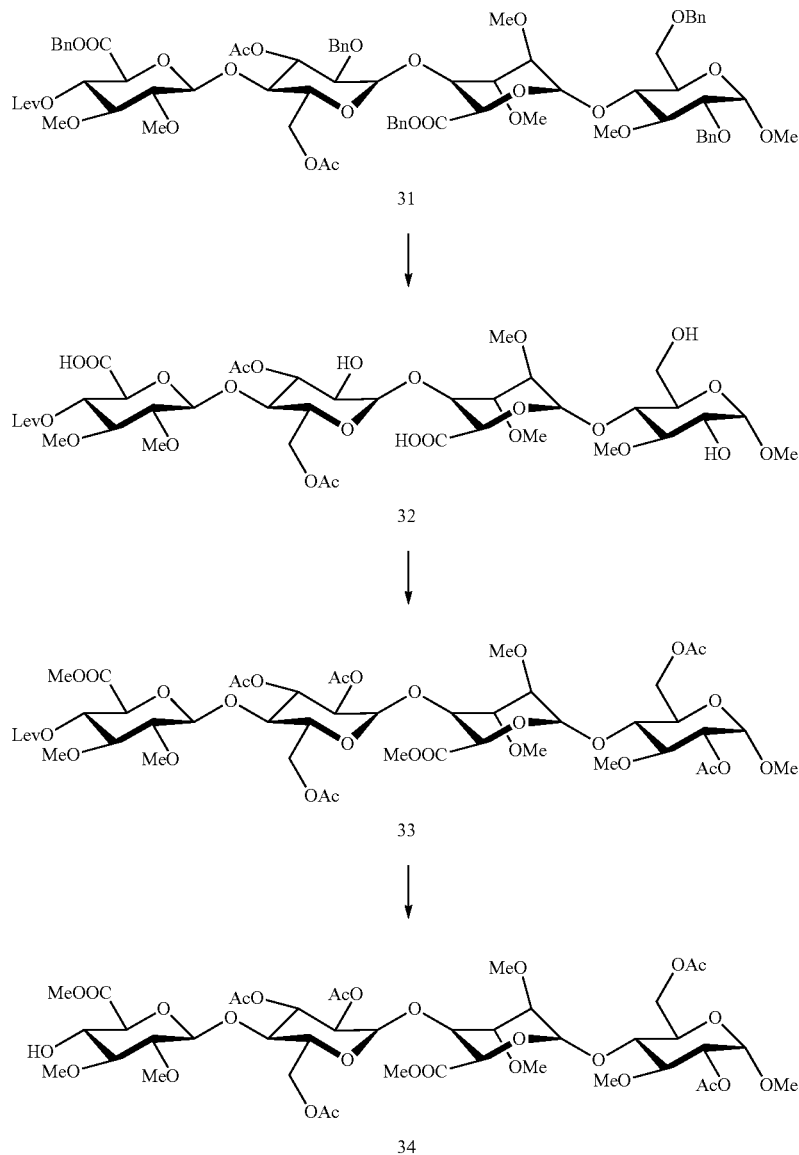

Preparation 28

Preparation of methyl (4-O-levulinyl-2,3-di-O-methyl-β-D-glucopyranosyluronic acid)-(1→4)-(3,6-di-O-acetyl-α-D-glucopyranosyl)-(1→4)-(2,3-di-O-methyl-α-L-idopyranosyluronic acid)-(1→4)-3-O-methyl-α-D-glucopyranoside (No. 32)

A solution of compound 31 (4.50 g, 3.02 mmol), prepared by analogy with Preparation 31 described in the patent application published under the number WO 99/36443, in 72 ml of an ethyl acetate/tert-butanol mixture [1/1 (v/v)] is treated under a pressure of hydrogen (4 bar) in the presence of 10% palladium-on-charcoal (9.0 g) for 6 hours. After filtration and concentration, the compound 32 obtained is used directly in the following step without purification.

Preparation 29

Preparation of methyl (methyl 4-O-levulinyl-2,3-di-O-methyl-β-D-glucopyranosyluronate)-(1→4)-(2,3,6-tri-O-acetyl-α-D-glucopyranosyl)-(1→4)-(methyl 2,3-di-O-methyl-α-L-idopyranosyluronate)-(1→4)-2,6-di-O-acetyl-3-O-methyl-α-D-glucopyranoside (No. 33)

To a solution of compound 32 (1.09 g, 1.13 mmol) in anhydrous N,N-dimethylformamide (15 ml) are added, at 0° C., potassium hydrogen carbonate (1.13 g) and then methyl iodide (1.4 ml). After stirring for 16 hours at room temperature, the reaction medium is cooled to 0° C. Dimethylaminopyridine (44 mg) and then acetic anhydride (2.4 ml) are then successively added. The mixture is stirred for 16 hours. After neutralizing the excess acetic anhydride, the mixture is diluted with ethyl acetate. The organic phase is successively washed with 10% potassium hydrogen sulfate solution, with water and then with saturated sodium hydrogen carbonate solution and with water. The organic phase is then dried over anhydrous sodium sulfate, filtered and then evaporated to dryness. The residue obtained is subjected to acetylation again under the standard conditions (acetic anhydride, dimethylaminopyridine, triethylamine in dichloromethane). After work-up, the residue is purified by chromatography on a column of silica gel [12/2.5/2.5 (v/v/v) cyclohexane/ethyl acetate/ethanol] to give 0.910 g of compound 33.

TLC on silica gel, toluene/acetone [2/1 (v/v)]: Rf=0.49

Preparation 30

Preparation of methyl (methyl 2,3-di-O-methyl-β-D-glucopyranosyluronate)-(1→4)-(2,3,6-tri-O-acetyl-α-D-glucopyranosyl)-(1→4)-(methyl 2,3-di-O-methyl-α-L-idopyranosyluronate)-(1→4)-2,6-di-O-acetyl-3-O-methyl-α-D-glucopyranoside (No. 34)

Compound 33 (0.884 g, 0.793 mmol) is dissolved in 160 ml of a toluene/ethanol mixture [1/1 (v/v)]. Hydrazine acetate (0.365 mg) is added. After stirring for 5 hours at room temperature, the reaction medium is concentrated to dryness. The residue is dissolved in dichloromethane. The organic phase is successively washed with 2% sodium hydrogen carbonate solution and with water, and then dried over anhydrous sodium sulfate, filtered and evaporated to dryness. After chromatography on a column of silica gel [5/3 (v/v) toluene/acetone], 0.696 g of compound 34 is obtained.

TLC on silica gel, toluene/acetone [2/1 (v/v)]: Rf=0.37

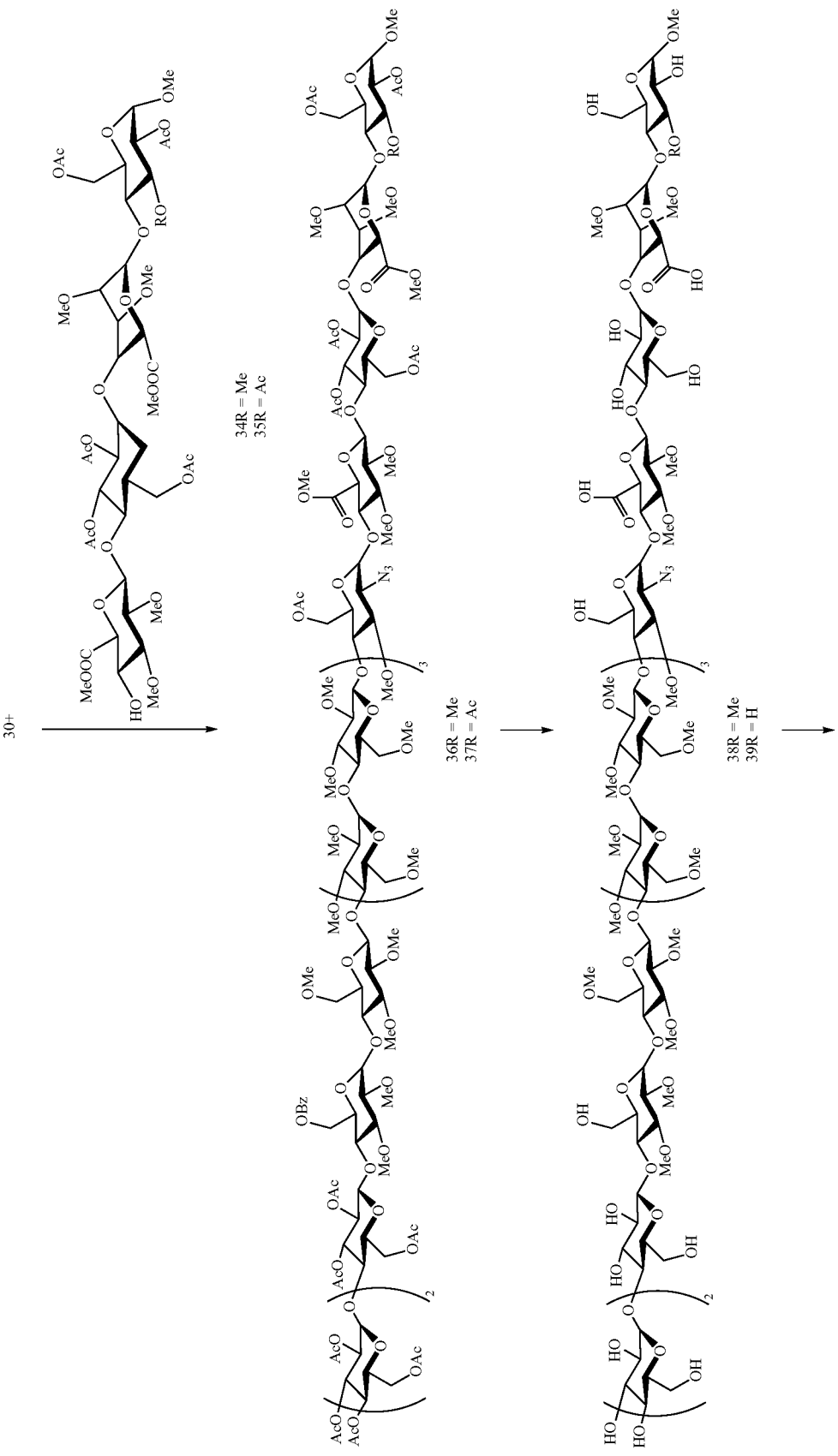

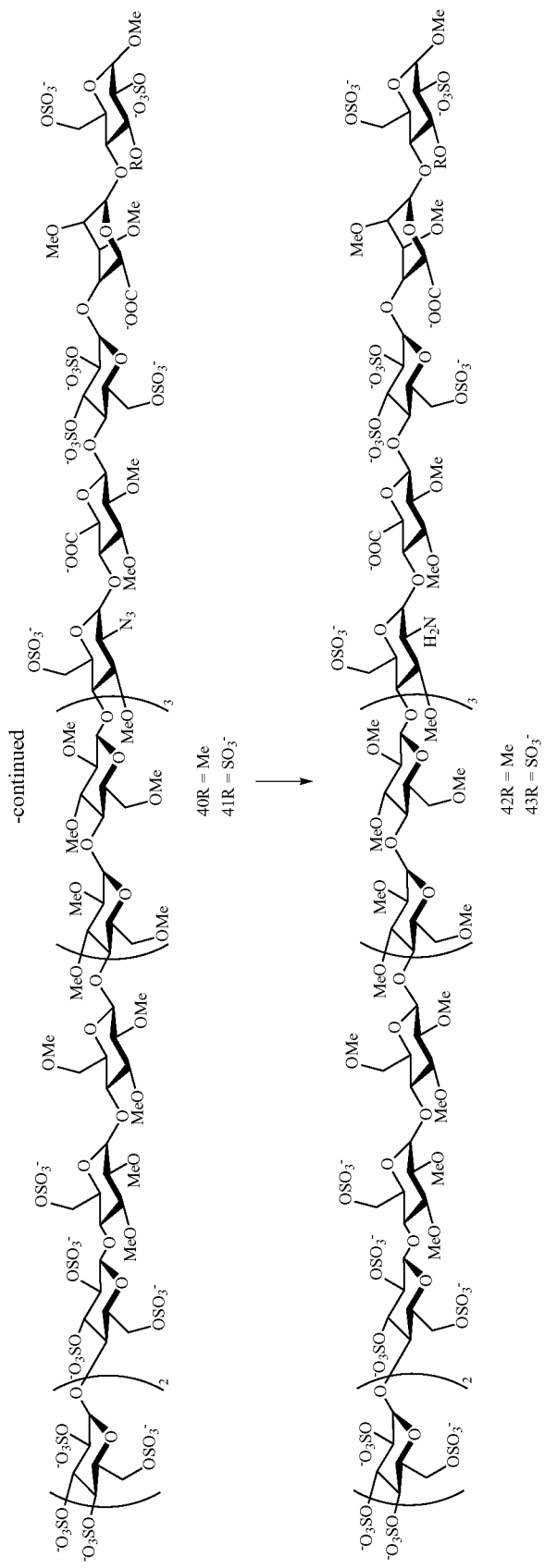

Preparation 31

Preparation of methyl (2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(6-O-acetyl-2-azido-2-deoxy-3-O-methyl-α-D-glucopyranosyl)-(1→4)-(methyl 2,3-di-O-methyl-β-D-glucopyranosyluronate)-(1→4)-(2,3,6-tri-O-acetyl-α-D-glucopyranosyl)-(1→4)-(methyl 2,3-di-O-methyl-α-L-idopyranosyluronate)-(1→4)-2,6-di-O-acetyl-3-O-methyl-α-D-glucopyranoside (No. 36)

The imidate compound 30 (170 mg, 56 μmol) obtained in Preparation 27, and compound 34 (114 mg, 112 μmol) obtained in Preparation 30 are dissolved in 2.5 ml of a dichloromethane/diethyl ether mixture [1/2 (v/v)]. After addition of powdered 4 Å molecular sieves, the mixture is cooled to −20° C. and a 0.1M solution of trimethylsilyl trifluoromethanesulfonate in dichloromethane (84 μl) is added. After 40 minutes, the mixture is neutralized by addition of solid sodium hydrogen carbonate. After filtration and concentration, the residue is purified by chromatography on Sephadex® LH60 gel, followed by chromatography on a column of silica gel [diethyl ether/ethanol (17/2 v/v)] to give 123 mg of compound 36.

Mass: "ESI" method, positive mode: chemical mass=3890.87; experimental mass: 3890.46±0.68 a.m.u.

TLC on silica gel, diethyl ether/ethanol [17/2 (v/v)]: Rf=0.40

Preparation 32

Preparation of methyl (2,3,4,6-tetra-O-acetyl-α-D-glucopyranosyl)-(1→4)-(2,3,6-tri-O-acetyl-α-D-glucopyranosyl)-(1→4)-(2,3,6-tri-O-acetyl-β-D-glucopyranosyl)-(1→4)-(6-O-benzoyl-2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(6-O-acetyl-2-azido-2-deoxy-3-O-methyl-α-D-glucopyranosyl)-(1→4)-(methyl 2,3-di-O-methyl-β-D-glucopyranosyluronate)-(1→4)-(2,3,6-tri-O-acetyl-α-D-glucopyranosyl)-(1→4)-(methyl 2,3-di-O-methyl-α-L-idopyranosyluronate)-(1→4)-2,3,6-tri-O-acetyl-α-D-glucopyranoside (No. 37)

The imidate compound 30 obtained according to Preparation 27 (95 mg, 0.031 mmol) and compound 35 (65.4 mg, 0.062 mmol) obtained in Preparation 42 of the patent application published under the number WO 02/24754 are dissolved in 1.5 ml of a dichloromethane/diethyl ether mixture [1/2 (v/v)]. After addition of powdered 4 Å molecular sieves, the mixture is cooled to −20° C. and a 0.1M solution of trimethylsilyl trifluoromethanesulfonate in dichloromethane (47 μl) is added. After 40 minutes, the mixture is neutralized by addition of solid sodium hydrogen carbonate. After filtration and concentration, the residue is purified by chromatography on Sephadex LH60 gel (2 chromatographies were performed) to give 68 mg of compound 37.

Mass: "ESI" method, positive mode: chemical mass=3918.88; experimental mass: 3919.35±0.71 a.m.u.

TLC on silica gel, cyclohexane/ethyl acetate/ethanol [3/1/1 (v/v/v)]: Rf=0.53

Preparation 33

Preparation of methyl (α-D-glucopyranosyl)-(1→4)-(α-D-glucopyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(2-azido-2-deoxy-3-O-methyl-α-D-glucopyranosyl)-(1→4)-(2,3-di-O-methyl-β-D-glucopyranosyluronic acid)-(1→4)-(α-D-glucopyranosyl)-(1→4)-(2,3-di-O-methyl-α-L-idopyranosyluronic acid)-(1→4)-3-O-methyl-α-D-glucopyranoside (No. 38)

30% aqueous hydrogen peroxide solution (3.9 ml) is added, at −5° C., to a solution of compound 36 (111 mg) obtained in Preparation 31 in tetrahydrofuran (4.6 ml). After stirring for 5 minutes, aqueous 0.7M lithium hydroxide solution (1.8 ml) is added dropwise. The reaction mixture is stirred for 1 hour at −5° C. and then for 4 hours at 0° C. and finally for 16 hours at room temperature. The reaction mixture is deposited on a column of fine Sephadex® G-25 (5×100 cm) eluted with water. The fractions containing the expected compound are combined, concentrated and deposited on a column of Dowex® AG 50 WX4 H⁺ resin (1.9 ml). The compound is collected at 0° C. and concentrated to give 72.1 mg of compound 38.

TLC on silica gel, ethyl acetate/pyridine/acetic acid/water [16/12/2.6/7 (v/v/v/v)]: Rf=0.60.

Preparation 34

Preparation of methyl (α-D-glucopyranosyl)-(1→4)-(α-D-glucopyranosyl)-(1→4)-(β-D-glucopyranosyl)-(1→4)-(2,3-di-O-methyl-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(2-azido-2-deoxy-3-O-methyl-α-D-glucopyranosyl)-(1→4)-(2,3-di-O-methyl-β-D-glucopyranosyluronic acid)-(1→4)-(α-D-glucopyranosyl)-(1→4)-(2,3-di-O-methyl-α-L-idopyranosyluronic acid)-(1→4)-α-D-glucopyranoside (No. 39)

30% aqueous hydrogen peroxide solution (2.2 ml) is added, at −5° C., to a solution of compound 37 (60 mg) in tetrahydrofuran (5.5 ml). After stirring for 5 minutes, aqueous 0.7M lithium hydroxide solution (1 ml) is added dropwise. The reaction mixture is stirred for 1 hour at −5° C., then for 4 hours at 0° C. and finally for 16 hours at room temperature. The mixture is neutralized with 1M hydrochloric acid solution. The solution is deposited on a column of fine Sephadex® G-25 (5×100 cm) eluted with water. The fractions containing the expected compound are combined, concentrated and deposited on a column of Dowex® AG 50 WX4 H⁺ resin. The compound is collected at 0° C. and concentrated to give 37.5 mg of compound 39.

TLC on silica gel, ethyl acetate/pyridine/acetic acid/water [16/12/2.6/7 (v/v/v/v)]: Rf=0.36.

Preparation 35

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]$_3$-(2-azido-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-3-O-methyl-2,6-di-O-sulfonato-α-D-glucopyranoside, sodium salt (No. 40)

Just before using it, compound 38 obtained in Preparation 33 is co-distilled with N,N-dimethylformamide (3×2 ml). To a solution of compound 38 (70.3 mg, 22.8 μmol) in N,N-dimethylformamide (2 ml) is added sulfur trioxide-triethylamine complex (351 mg). The mixture is stirred for 16 hours at 55° C. in the absence of light. The mixture, cooled to 0° C., is added dropwise to a solution of sodium hydrogen carbonate in water. The resulting mixture is stirred for 16 hours at room temperature and concentrated to dryness. The residue, dissolved in water, is deposited on a column of fine Sephadex G-25 eluted with 0.2M sodium chloride. The fractions containing the product are concentrated and desalified using the same column eluted with water. After freeze-drying, 103 mg of compound 40 are obtained.

Mass: "ESI" method, negative mode: chemical mass=4864.82; experimental mass: 4862.90±0.21 a.m.u.

Preparation 36

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-(α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]$_3$-(2-azido-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt (No. 41)

Compound 39 (33 mg, 0.017 mmol) obtained in Preparation 34 is converted into compound 41 according to the procedure described in Preparation 35. After concentration, 40 mg of compound 41 are obtained.

Mass: "ESI" method, negative mode: chemical mass=4952.83; experimental mass: 4950.19±0.55 a.m.u.

Preparation 37

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]$_3$-(2-amino-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-3-O-methyl-2,6-di-O-sulfonato-α-D-glucopyranoside, sodium salt (No. 42)

A solution of compound 40 (93.8 mg) obtained in Preparation 35 in a mixture of tert-butanol (1.2 ml) and water (1.8 ml) is treated under a pressure of hydrogen (5 bar) in the presence of 10% palladium-on-charcoal (28 mg) at 40° C. for 4 hours. After filtration (Millipore® LSWP 5 μm filter), the solution is concentrated to dryness to give 93 mg of compound 42.

Preparation 38

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]$_3$-(2-amino-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt (No. 43)

Compound 41 (40.8 mg) obtained in Preparation 36 is converted into compound 43 according to the procedure described in Preparation 37. After concentration, 42.3 mg of compound 43 are obtained.

Mass: "ESI" method, negative mode: chemical mass=4926.84; experimental mass: 4924.07±0.36 a.m.u.

Example 1

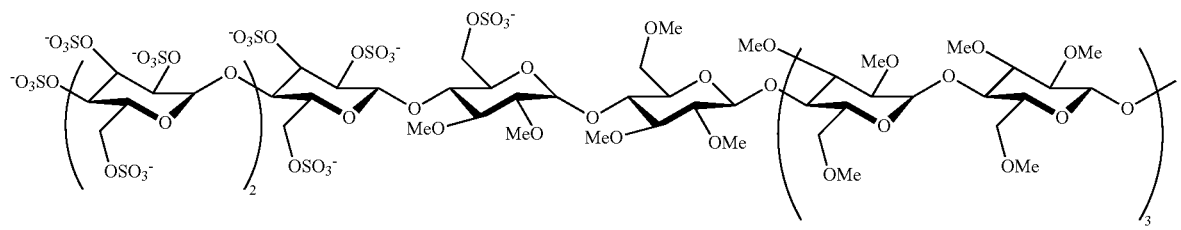

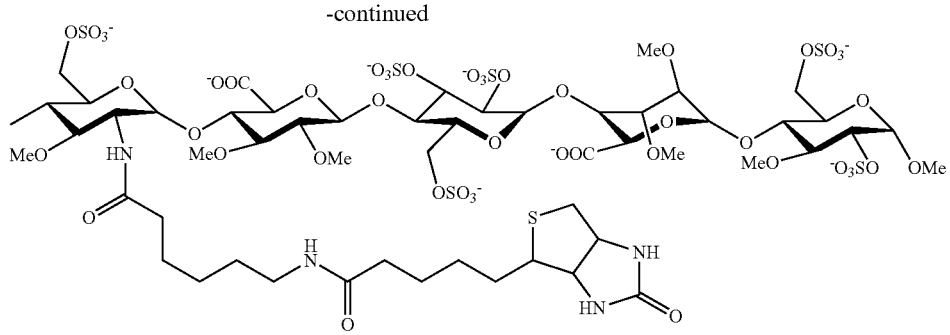

Example 2

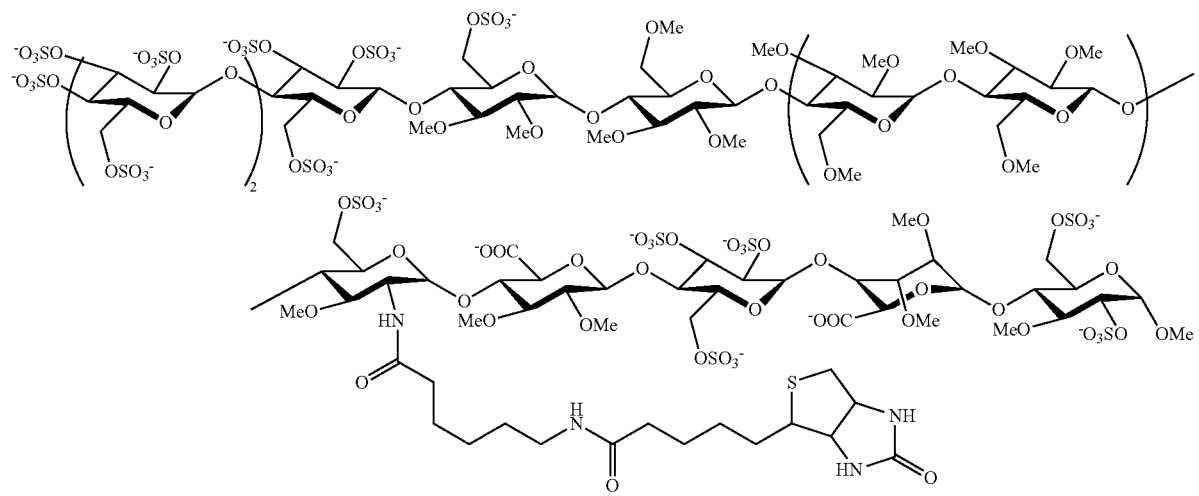

Example 1

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(2-[N-(6-biotinamidohexanoyl)]-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-3-O-methyl-2,6-di-O-sulfonato-α-D-glucopyranoside, sodium salt Compound 42 (20 mg, 4.13 μmol) obtained in Preparation 37 is dissolved in aqueous 0.5% sodium hydrogen carbonate solution (1.7 ml). A solution of sulfosuccinimide 6-(biotinamido)hexanoate (23 mg, 41.3 μmol) in 0.5% sodium hydrogen carbonate solution (100 μL) is added dropwise thereto. After stirring for 16 hours at room temperature, aqueous 1M sodium hydroxide solution is added and the mixture is stirred for 1 hour. The reaction mixture is deposited on a column of fine Sephadex® G-25 (5×100 cm) eluted with aqueous 0.2M sodium chloride solution. The fractions containing the product are concentrated and desalified using the same column eluted with water. After freeze-drying, 21.2 mg of the compound of Example 1 are obtained.

Mass: "ESI" method, negative mode; monoisotopic mass=5174.38; chemical mass=5178.28; experimental mass=5177.69±0.52 a.m.u.

Example 2

Preparation of methyl (2,3,4,6-tetra-O-sulfonato-α-D-glucopyranosyl)-(1→4)-(2,3,6-tri-O-sulfonato-α-D-glucopyranosyl)-(1→4)-(2,3,6-tri-O-sulfonato-β-D-glucopyranosyl)-(1→4)-(2,3-di-O-methyl-6-O-sulfonato-α-D-glucopyranosyl)-(1→4)-(2,3,6-tri-O-methyl-β-D-glucopyranosyl)-(1→4)-[(2,3,6-tri-O-methyl-α-D-glucopyranosyl)-(1→4)—O-(2,3,6-tri-O-methyl-β-D-glucopyranosyl)-(1→4)]₃-(2-[N-(6-biotinamidohexanoyl)]-2-deoxy-3-O-methyl-6-O-sulfonato-α-D-glucopyranosyl)-(1→4)-(2,3-di-O-methyl-β-D-glucopyranosyluronic acid)-(1→4)-(2,3,6-tri-O-sulfonato-α-D-glucopyranosyl)-(1→4)-(2,3-di-O-methyl-α-L-idopyranosyluronic acid)-(1→4)-2,3,6-tri-O-sulfonato-α-D-glucopyranoside, sodium salt Compound 43 (19.1 mg) obtained according to Preparation 38 is converted into compound 45 according to the procedure described in Example 1. After freeze-drying, 18.1 mg of the compound of Example 2 are obtained.

Mass: "ESI" method, negative mode: monoisotopic mass=5262.31; chemical mass=5266.30; experimental mass: 5263.93±0.38 a.m.u.

What is claimed is:

1. A method of treating a pathology consecutive to a modification in the homeostasis of the clotting system appearing during disorders of the cardiovascular and cerebrovascular system, comprising: administering to a patient in need thereof an effective amount of a biotinylated hexadecasaccharide of general formula I:

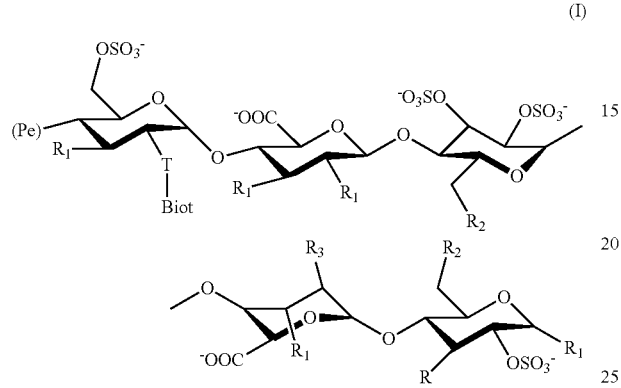

(I)

in which:

T represents a sequence $T_1$ or $T_2$ having the following formulae:

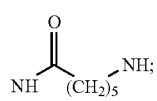

(T$_1$)

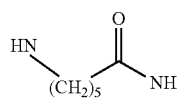

(T$_2$)

Biot represents the group:

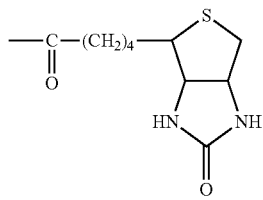

R represents a ($C_1$-$C_6$)alkoxy radical, or an —$OSO_3^-$ radical;

$R_1$ represents a ($C_1$-$C_6$)alkoxy radical, or an —$OSO_3^-$ radical;

$R_2$ represents a ($C_1$-$C_6$)alkoxy radical or an —$OSO_3^-$ radical;

$R_3$ represents a ($C_1$-$C_6$)alkoxy radical, or an —$OSO_3^-$ radical, or alternatively $R_3$ constitutes an —O—$CH_2$— bridge, the —$CH_2$— group being linked to the carbon atom bearing the carboxylic function on the same ring; and Pe represents a saccharide sequence having the following formula:

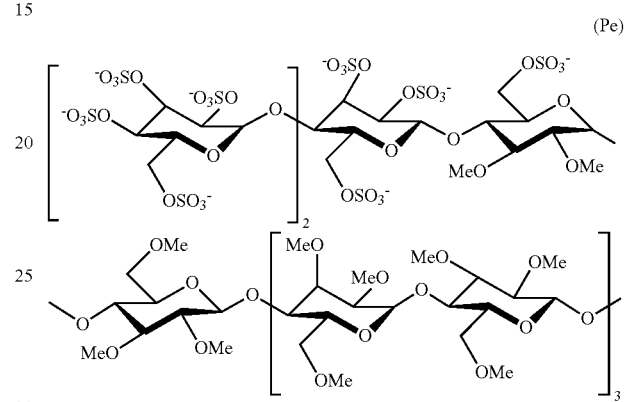

(Pe)

and a pharmaceutically acceptable salt thereof;

wherein the pathology is selected from: unstable angina, apoplexy, post-angioplasty restenosis, thromboembolic disorders associated with post-thrombolysis rethrombosis, infarction, dementia of ischaemic origin, peripheral arterial diseases, blood dialysis, auricular fibrillations, thrombosis during the use of vascular prostheses for aorto-coronary bypasses, thromboembolic pathologies of venous origin, pulmonary embolism, thrombotic complications observed following surgical operations, the development of tumours or the disruption of clotting, induced by bacterial, viral or enzymatic activators and thrombosis associated with endarterectomy or the insertion of endovascular prostheses.

2. A method of treating a prosthesis, comprising: covering the prosthesis with a biotinylated hexadecasaccharide according to claim 1.

3. A method of performing an endarterectomy performed with a porous balloon, comprising: using a biotinylated hexadecasaccharide according to claim 1 as an adjuvant.

* * * * *